United States Patent [19]

Skipper

[11] 3,955,959

[45] May 11, 1976

[54] HERBICIDE FOR USE IN TRANSPLANTED RICE

[75] Inventor: Horace Dean Skipper, Clemson, S.C.

[73] Assignee: Monsanto Company, St. Louis, Mo.

[22] Filed: July 12, 1974

[21] Appl. No.: 488,096

[52] U.S. Cl. .................................................. 71/118
[51] Int. Cl.² ........................................... A01N 9/20
[58] Field of Search ....................................... 71/118

[56] References Cited
UNITED STATES PATENTS 3,547,620    12/1970    Olin ....................................... 71/118
3,663,200    5/1972    Olin ....................................... 71/118

*Primary Examiner*—Glennon H. Hollrah
*Attorney, Agent, or Firm*—William I. Andress; Donald W. Peterson

[57] ABSTRACT

N-(butoxymethyl)-6'-tert-butyl-2-chloro-o-acetotoluidide is used as a broad-spectrum weed control herbicide while providing a high degree of crop safety toward transplanted rice cultures.

15 Claims, No Drawings

HERBICIDE FOR USE IN TRANSPLANTED RICE

BACKGROUND OF THE INVENTION

1. Field of the Invention

The invention herein pertains to the field of herbicides. In more particular the invention pertains to the field of herbicides suitable for use against undesired vegetation in the presence of transplanted rice. In still more particular, this invention pertains to the preemergent or postemergent use of N-(butoxymethyl)-640 -tert-butyl-2-chloro-o-acetotoluidide against monocotyledonous and dicotyledonous weeds, e.g., grasses, sedges and broadleaf weeds, in the presence of transplanted rice.

2. Description of the Prior Art

The food crop rice is the major food staple for approximately 60% of the world's population. This crop is grown on an estimated 326 million acres (about 131.9 million hectares). Of the total rice coverage under cultivation, it is estimated that 70%, or about 229 million acres (about 92.7 million hectares), is the transplanted rice culture, and the remaining 30%, or about 97 million acres (about 39.3 million hectares), is the direct-seeded rice culture (including drill-seeded, broadcastsown, puddle-seeded, water-seeded and upland). Accordingly, much effort is required to produce sufficient rice to meet the widespread demand therefor.

Most of the rice lands under cultivation are weeded by hand, hence, much human effort is expended in raising rice. It has been estimated that to manually remove weeds from transplanted rice fields requires 120–160 man hours per acre (300–400man hours per hectare). Hand-weeding in direct-seeded rice is even more demanding. Thus, with 326 million acres in rice production and the ever-increasing migration of farm workers to the cities, especially in developing countries, rice herbicides are achieving an even greater importance in helping to raise sufficient rice to meet the needs of those dependent upon it.

A number of herbicides have been introduced on the market in an effort to provide chemical weeding of rice fields. However, rice herbicides (i.e., herbicides useful against weeds in rice fields) of the prior art have met with only more or less limited success, because of certain inherent limitations. For example, it is known that the following prior art rice herbicides have the indicated disadvantages: (1) 3,4-dichloropropionanilide has strict requirements as to the method of application and water management; (2) 2-chloro-N-(butoxymethyl)-2',6'-diethylacetanilide, and the chlorinated phenyl nitrophenyl ethers, e.g., 2,4-dichloro- and 2,4,6-trichlorophenyl-4-nitrophenyl ethers, or a mixture of the latter with p-chlorobenzyl-N,N-diethylthiolcarbamate have only brief periods of application; (3) S-ethyl hexahydro-1H-azepine-1-carbothioate has a narrow spectrum of weed control; and (4) the phenoxies, 2-tert-butyl-4-(2,4-dichloro-5-isopropyloxyphenyl)-5-oxo-1,3,4-oxadiazoline and mixtures of p-chlorobenzyl-N,N-diethylthiolcarbamate with 2,4-bis (ethylamino)-6-(methylthio)-s-triazine have marginal crop safety. Combinations of the foregoing disadvantages are also found in prior art rice herbicides.

Among herbicidal compounds of the prior art which are most closely related in structure to the compound of interest in the present invention are the N-oxaalkylene-α-haloacetanilides. Included within these prior art acetanilide compounds are those wherein the positions ortho to the anilide nitrogen atom are both unoccupied by any substituents, or one or both ortho positions are occupied by various radicals including straight or branched-chain alkyl radicals, and the oxaalkylene substituent on the anilide nitrogen atom has one or more carbon atoms in the alkylene moiety adjacent to the nitrogen atom. By "oxaalkylene" is meant an alkylene radical one of whose methylene groups has been replaced with an oxa oxygen atom (—O—) resulting in a radical of the structure —CH$_2$—O—CH$_2$—.

Illustrative of the α-haloacetanilide herbicidal compounds of the above types are such compounds as are described in U.S. Pat. Nos. 2,863,752, 3,442,945, 3,547,620, 3,663,200 and British Pat. No. 1,008,851, all of which are assigned to applicant's assignee herein. In said U.S. '752 patent, the ortho positions may be both occupied by hydrogen atoms or one of these positions may be occupied with, inter alia, an alkyl radical having up to four carbon atoms. Said British Pat. No. 1,008,851 discloses N-oxaalkylene compounds wherein one of the ortho positions may be an alkyl group and the other ortho position must be occupied by a tert-alkyl group. Both of said U.S. '752 and British '851patents exemplify the above types of compounds with no less than two alkylene carbon atoms in the oxaalkylene moiety of the compounds. Moreover, neither of the '752 nor '851 patents disclose any herbicidal utility with respect to rice of any culture.

The above U.S. Pat. No. 3,663,200 discloses the use of N-butoxymethyl-2',6'-diethyl-2-chloroacetanilide (common name —butachlor) and/or its N-butoxyethyl homolog as rice herbicides for inhibiting the growth of other grasses, e.g., barnyardgrass. In field tests comparing herbicidal properties of butachlor, the active ingredient of a commercial rice herbicide with those of the compound of the present invention, it was found that the latter is superior to the former in two important aspects, viz. (1) the application rate use requirements are from 3 to 6 (or more) times less, and (2) the time span of application to the weeds is much greater, i.e., the compound of this invention may be effectively applied as late as the 2–2.5 leaf stage of growth, whereas butachlor is applied at the 1 leaf stage of growth to achieve optimum weed control.

Said U.S. Pat. No. 3,663,200 patent is a continuation-in-part of said U.S. Pat. No. 3,547,620 patent. The compound of use in the present invention is also disclosed as a herbicidal compound in said '620, as well as in said '945 patent. It is also disclosed in Table I in each of said '620 and '945 patents that the compound of Example 4 in each of said patents (the same compound of the present invention, but with slightly different nomenclature) was tested for herbicidal activity with respect to a variety of weeds and crops, including "rice". However, the rice plants used in the '620 and '945 patents were direct-seeded rice culture as indicated by the disclosed method of planting and growing the plants. As shown in Table I of each of said '620 and '945 patents, the compound of Example 4 therein exhibited severe phytotoxicity with respect to direct-seeded rice plants under the conditions of the test and at the concentrations used, i.e., 1.0 lb/ac (ca. 1.12kgs/ha) and 0.25 lb/ac (ca. 0.28 kg/ha). Accordingly, that disclosure standing alone would tend to suggest to those skilled in the art that the compound of said Example 4 would be unsatisfactory for use as a rice herbicide, at least, at the rates tested.

SUMMARY OF THE INVENTION

The present invention relates to a method for selectively inhibiting (including complete control of) certain undesirable vegetation in the presence of transplanted rice. The method of this invention comprises applying to the growth medium of and/or said undesirable vegetation and transplanted rice a herbicidally effective amount of the compound N-(butoxymethyl)-6'-tert-butyl-2-chloro-o-acetotoluidide.

Undesirable vegetation against which said compound has shown results ranging from fair to excellent control includes monocotyledons and dicotyledons such as grasses, sedges and broadleaf weeds.

Among said grasses effectively treated to date are the following: *Brachiaria platyphylla*, *Digitaria* spp, *Echinochloa* spp, *Eleusine indica*, *Leptochloa* spp and *Setaria* spp.

Among said sedges effectively treated to date are the following: *Cyperus difformis*, *Cyperus iria*, *Cyperus serotinus*, *Eleocharis acicularis*, *Eleocharis kuroguwai*, *Fimbristylis* spp, *Scirpus hotarui* and *Scirpus* spp (bulrush).

Among monocotyledonous broadleaf weeds effectively treated to date are *Alisma canaliculatum*, *Aneilema japonica*, *Monochoria vaginalis*, *Commelina communis*, and among dicotyledonous broadleaf weeds, *Ammannia* spp, *Amaranthus retroflexus*, *Elatine triandra*, *Jussiaea decurrens*, *Lindernia pyxidaria*, *Rotala Sphenoclea zeylanica* and *Partulaca oleracea*.

The herbicide according to this invention is applied at rate corresponding to from about 0.05 lb/acre to about 4 or more lbs/acre (about 0.06 kg/hectare to about 4.58 kgs/hectare or more). Preferred application rates range from about 0.25 to 1.5 lbs/acre (i.e., from about 0.28 to about 1.68 kgs/hectare). The most preferred application rate is about 0.5 lb/acre (about 0.56 kg/hectare).

The herbicide of this invention can be applied preemergently (i.e., with respect to emergence of undesired vegetation), both by incorporation into the soil or by application to the surface thereof, or to the surface of the water into which the rice seedlings are transplanted, or postemergently, i.e., in direct contact with said undesired vegetation.

Contrary to and in spite of the apparent negative disclosure in the above-mentioned '620 and '945 patents relative to the herbicidal effect of the compound of Example 4 of said patents with respect to direct-seeded rice, applicant has unexpectedly discovered that N-(butoxymethyl)-6'-tert-butyl-2-chloro-o-acetotoluidide has superior herbicidal activity with respect to undesired vegetation in the presence of transplanted rice with negligible crop injury, i.e., a high degree of crop safety at recommended use rates.

Therefore, it is an object of the present invention to provide a transplanted rice herbicide which has high unit activity with respect to a broad spectrum of noxious weeds, while maintaining crop safety with respect to said transplanted rice at practical rates of use.

It is a further object of this invention to provide a transplanted rice herbicide which may be applied over a relatively prolonged period of application, simply and without need for strict requirements of application or water management.

A concomitant result of achieving the above objectives is increased economy based on use of less herbicide to control weeds.

The above and other objects will become more apparent in view of the detailed description given below.

DESCRIPTION OF PREFERRED EMBODIMENTS

The present invention is exemplified herein by tests in laboratory-greenhouse investigations and by field tests in countries in which transplanted rice is a major crop, i.e., Japan, Republic of Korea, Taiwan and the Philippine Islands. Results of such tests are presented in the tables below.

For illustrative and comparative purposes, particular consideration has been given to comparisons between the herbicide of use in this invention and the above-mentioned commercial herbicide, because the active ingredient of the latter, butachlor, is the most closely related in chemical structure of any prior art rice herbicidal compound.

In the tables below, the various plant species tested are identified according to the following abbreviations:

| | |
|---|---|
| Aj — *Aneiliema japonica* | Ek — *Eleocharis kuroguwai* |
| Ar — *Amaranthus retroflexus* | Ei — *Eleusine indica* |
| Bp — *Brachiaria platyphylla* | Et — *Elatine triandra* |
| Cc — *Commelina communis* | Fl — *Fimbristylis littoralis* |
| Cd — *Cyperus difformis* | Jd — *Jussiaea decurrens* |
| Ce — *Cyperus esculentus* | Lp — *Lindernia pyxidaria* |
| Ci — *Cyperus iria* | Mv — *Monochoria vaginalis* |
| Cyp — *Cyperus* spp | Po — *Portulaca oleracea* |
| Cs — *Cyperus serotinus* | Ri — *Rotala indica* |
| Ds — *Digitaria sanguinalis* | Sa — *Sagittaria aginashi* |
| Ec — *Echinochloa crusgalli* | Sp — *Sagittaria pygmaea* |
| Ecol — *Echinochloa colonum* | Sh — *Scirpus hotarui* |
| Eo — *Echinochloa oryzicola* | Sz — *Sphenoclea zeylanica* |
| Ea — *Eleocharis acicularis* | |

The procedure for preparing the active ingredient of the herbicide of this invention is described in detail in the above-mentioned U.S. Pat. Nos. 3,442,945 and 3,547,620. The procedure for preparing the active ingredient (butachlor) in the prior art herbicide is also described in said '945 and '620 patents, as well as in the above-mentioned U.S. Pat. No. 3,663,200. The descriptions of those procedures are incorporated herein by reference. In general terms, the said active ingredients are prepared by reacting the appropriate substituted methylene aniline with chloroacetyl chloride to produce the corresponding N-chloromethyl-α-chloroacetanilide intermediate product which is then reacted with n-butanol to produce the final product.

In the tests described in the tables below, the herbicides were formulated and used in granular form in conventional manner. The granular herbicide embodiment of this invention comprised 2.5% active ingredient (i.e., N-(butoxymethyl)-6'- tert-butyl-2-chloro-o-acetotoluidide), 95.24% clay (calcined attapulgite), 2.0% dipropylene glycol as stabilizer and the balance inert material. The commercial herbicide used was a granular product having 5% active ingredient.

In the field tests of the herbicide of this invention with transplanted rice, the rice seedlings were grown in conventional manner, by seeding the rice in a typical seedbed of sandy loam to clay soil of the country wherein the test was conducted. For laboratory and greenhouse work the seedlings were obtained by seeding rice in a mixture of soil, e.g., Ray silt loam, and peat in wood flats. For purposes of testing the herbicides on younger rice seedlings (infant or Dapog) the rice was usually allowed to grow for 6–15 days before lifting for transplanting. Older (ordinary) rice plants were usually grown for a period of about 2–3 weeks, or as much as about 7 weeks before lifting. Since the period of growth is dependent upon climatic conditions, a better measure of when to transplant the rice seedling is the leaf stage of growth; for infant or Dapog rice the seedling is lifted at the 1.5–2 leaf stage of growth, and for ordinary seedlings at the 2.5–5 leaf stage. The seedlings were then transplanted to the test plots for evaluation of the herbicide for injury against weed species present with the transplanted rice. The herbicides were then applied to the growth medium of the weeds and transplant rice, either preemergent or postemergent with respect to the weeds and postemergent with respect to the transplanted rice. Application times are designated in the tables as "DAT", meaning "days after transplant". Application rates given in the tables refer to the amount of active ingredient used. Observations of herbicidal activities were made at different times as indicated for the several test results reported in the tables. Comparative yield results relative to hand weeded ("H.W.") and untreated ("Weedy") checks, or standards, are given in the tables. "Hand weeded" followed by "X", e.g., "3X" indicates that the test plots were hand weeded 3 times.

In the tables below, the herbicides used are identified by their active ingredients as follows:
A.   N-(butoxymethyl)-6'-tert-butyl-2-chloro-o-acetotoluidide (the compound of use in this invention).
B.   N-(butoxymethyl)-2',6'-diethyl-2-chloroacetanilide (butachlor).

EXAMPLE 1

In this example, comparative results are shown for the performance of Herbicides A and B in a field test for weed control in transplanted rice in silty clay loam soil at Iri, Korea.

In the field test 48 day-old seedlings (Watanabe variety) were transplanted to plots 2.5 × 6 m. seeded with the weed seeds indicated in Table 1. At 5 and 10 DAT periods, the herbicides were applied to the plants (now at the 1.2 and 2.0 leaf stage, respectively, of grass weed) at the indicated rate in kilograms per hectare (kg/ha). The weed control and rice injury results for 3 replications are reported in percentages as of the indicated times of observation. The percentages given in the "Perennials" column are based on the weight of the weeds at 63 DAT, i.e., 42 gms/3.6 m² for the weedy check.

Table 1

| Treatment | | | % Weed Control (av. of 36 and 63 DAT) | | | | | %Rice Injury | | Yield |
| | | | Grass | Sedge | Broadleaf weeds | | Perennials | | | (% of Hand- |
| Herbicide | DAT | Rate kg/ha | Eo | Ci | Mv | Aj | Ek and Sa | (21 DAT) | (42 DAT) | weeded Check) |
|---|---|---|---|---|---|---|---|---|---|---|
| A | 5 | .25 | 86 | 85 | 72 | 66 | 0 | 0 | 0 | 102 |
| " | " | .5 | 93 | 95 | 80 | 84 | 55 | 0 | 0 | 101 |
| " | " | 1.0 | 91 | 100 | 89 | 81 | 68 | 5 | 0 | 100 |
| " | " | 2.0 | 94 | 95 | 82 | 86 | 100 | 10 | 0 | 101 |
| " | 10 | .25 | 82 | 74 | 53 | 73 | 0 | 0 | 0 | 98 |
| " | " | .5 | 88 | 98 | 80 | 79 | 2 | 0 | 0 | 99 |
| " | " | 1.0 | 90 | 97 | 72 | 79 | 0 | 0 | 0 | 99 |
| " | " | 2.0 | 92 | 93 | 83 | 88 | 0 | 10 | 0 | 100 |
| B | 5 | 1.0 | 64 | 98 | 43 | 79 | 0 | 0 | 0 | 95 |
| " | " | 1.5 | 89 | 97 | 55 | 76 | 41 | 0 | 0 | 100 |
| " | " | 3.0 | 92 | 99 | 70 | 85 | 0 | 5 | 0 | 99 |
| " | 10 | 1.0 | 68 | 54 | 58 | 58 | 0 | 0 | 0 | 95 |
| " | " | 1.5 | 83 | 100 | 75 | 77 | 0 | 0 | 0 | 97 |
| " | " | 3.0 | 77 | 93 | 69 | 78 | 0 | 0 | 0 | 100 |
| Hand Weeded Check (3×) | | | 78 | 99 | 79 | 71 | 73 | 0 | 0 | 100 (5647 kg/ha) |
| Weedy (No./m²) Check | | | (78) | (19) | (30) | (9) | | 0 | 0 | 88 |

The conclusion derived from the above test results of this example was that Herbicide A was many times (usually at least 4 or 5 times) more active than Herbicide B. In this particular test, with respect to Herbicide A, although perenniaal control at 14 DAT and at rates less than 2 kgs/ha applied 5 DAT was considered less than adequate, the advantage over Herbicide B is clearly evident. In other tests, control of the perennial EK by Herbicide A has ranged from fair to good, whereas, activity against Sa remains generally weak. The slight early season injury to rice was outgrown.

There was a significant yield depression at the 1.0kg/ha rate of Herbicide B which is related to the lower weed control data.

EXAMPLE 2

In this example, comparative results from a field test are shown for weed control and rice yields from transplanted rice grown in clay loam soil at Chia Yi, Taiwan.

Rice seedlings (ordinary) of Tainan No. 5 variety (japonica) were transplanted at 19 days of growth. Granular formulations of Herbicides A and B were applied at the 1 leaf stage of grass weed (4 DAT) and 2.5 leaf stage of grass weed (10 DAT). Observations were made at 63 DAT and results reported in Table 2 as an average of 3 replications.

Table 2

| Treatment | | | Observations 63 DAT % Weed Control | | | % Crop Injury | | Yield |
| | | | Echinochloa | Cyperus | Monochoria | vigor | stand | (% of H.W. |
| Herbicide | DAT | Kg/ha | crusgalli | difformis | Vaginalis | | | Check) |
|---|---|---|---|---|---|---|---|---|
| A | 4 | .25 | 85 | 100 | 80 | 0 | 0 | 97 |
| " | " | .5 | 98 | 100 | 99 | 0 | 0 | 105 |
| " | " | 1.0 | 100 | 100 | 100 | 0 | 0 | 107 |
| " | " | 2.0 | 100 | 100 | 100 | 27 | 5 | 81 |

Table 2-continued

| Treatment | | | Observations 63 DAT %Weed Control | | | % Crop | Injury | Yield |
| Herbicide | DAT | Kg/ha | Echinochloa crusgalli | Cyperus difformis | Monochoria Vaginalis | vigor | stand | (% of H.W. Check) |
| --- | --- | --- | --- | --- | --- | --- | --- | --- |
| '' | 10 | .25 | 65 | 100 | 35 | 0 | 0 | 91 |
| '' | '' | .5 | 95 | 100 | 87 | 2 | 0 | 100 |
| '' | '' | 1.0 | 100 | 100 | 99 | 7 | 3 | 105 |
| '' | '' | 2.0 | 100 | 100 | 99 | 25 | 15 | 73 |
| B | 4 | 1.0 | 65 | 100 | 77 | 0 | 0 | 110 |
| '' | '' | 1.5 | 92 | 100 | 94 | 0 | 0 | 103 |
| '' | '' | 3.0 | 97 | 100 | 99 | 0 | 0 | 99 |
| '' | 10 | 1.0 | 77 | 100 | 65 | 0 | 0 | 97 |
| '' | '' | 1.5 | 78 | 100 | 78 | 0 | 0 | 98 |
| '' | '' | 3.0 | 98 | 100 | 89 | 0 | 0 | 99 |
| Hand Weeded (2×) | | | 98 | 100 | 99 | 0 | 0 | 100 (4320 kg/ha) |
| Weedy Check | (No./m²) | | (3) | (6) | (133) | 0 | 0 | 74 |

The field test according to this example resulted in a conclusion that Herbicide A was 3–6 fold more active and could be applied over a longer period of time than Herbicide B for control of *Echinochloa crusgalli* and *Monochoria vaginalis*. The latter weed is considered to be the number 1 weed in the first rice crop and the number 2 weed (after *Cyperus difformis*) in the second rice crop in Taiwan.

The use of Herbicide A at 2 kgs/ha resulted in a rice yield depression. However, this rate is about 4 times the expected use rate under the conditions prevailing in this example.

EXAMPLE 3

This example sets forth the comparative results of the performance of Herbicides A and B in a field test on Dapog transplanted rice at Muñoz, Philippines.

Eleven (11) day-old Dapog seedlings were transplanted and treated at 5 DAT and 14 DAT with Herbicides A and B. The plots were overseeded with *Echinochloa crusgalli* seeds at 2 kgs/ha prior to transplanting. Treatments were replicated four times. Weed control ratings were made at 3 and 6 weeks after transplanting; the observations shown in Table 3 were the 6-week observations.

higher rates produced considerable rice injury, yet, even at the highest rate tested, i.e., 2 kgs/ha, the rice yield was statistically similar to the hand weeded check. The 1 kg/ha rate of Herbicide B at 5 DAT was also significantly higher than the control.

Two points appear to stand out in this test: (1) with the conditions prevailing in this test, the range of rates were too high for completely bracketing the range of weed control at 5 DAT, and, (2) the rates were too low for optimum weed control at 14 DAT. The best solution would seem to be for an earlier application date.

The comparatively large yield increases in this test with the herbicide treatments must be attributed to both the imperfect weed control and the high weed pressure in the hand weeded check.

EXAMPLE 4

In this example comparative field tests were conducted with Herbicides A and B on ordinary transplanted rice at Muñoz, Philippines. The objective here was to compare results of herbicidal treatment on older transplant rice seedlings.

Twenty-one (21) day-old ordinary wet bed seedlings of the Fortuna variety were transplanted to field plots and Herbicides A and B applied at 5 DAT and 14 DAT.

Table 3

| Treatment | | | Observations-42 DAT % Weed control | | | Crop | Yield |
| Herbicide | DAT | Rate kg/ha | Grass Ec and Ecol | Sedges Cd, Ci, Fl | Broadleaf Mv,Sz | Injury (%) | (% of H.W. Check) |
| --- | --- | --- | --- | --- | --- | --- | --- |
| A | 5 | .25 | 100 | 100 | 100 | 0 | 182 |
| '' | '' | .5 | 100 | 100 | 100 | 0 | 177 |
| '' | '' | 1.0 | 100 | 100 | 100 | 40 | 139 |
| '' | '' | 2.0 | 100 | 100 | 100 | 50 | 104 |
| '' | 14 | .25 | 0 | 0 | 0 | 0 | 93 |
| '' | '' | .5 | 50 | 70 | 60 | 0 | 98 |
| '' | '' | 1.0 | 50 | 70 | 60 | 0 | 113 |
| '' | '' | 2.0 | 90 | 70 | 60 | 80 | 98 |
| B | 5 | 1.0 | 100 | 100 | 100 | 0 | 142 |
| '' | '' | 1.5 | 100 | 100 | 100 | 0 | 107 |
| '' | '' | 3.0 | 100 | 100 | 100 | 0 | 101 |
| '' | 14 | 1.0 | 0 | 0 | 0 | 0 | 83 |
| '' | '' | 1.5 | 0 | 0 | 0 | 0 | 89 |
| '' | '' | 3.0 | 60 | 70 | 70 | 0 | 93 |
| H.W. Check (2×) | | | 100 | 80 | 80 | 0 | 100 (3,075 kg/ha) |
| Weedy Check (No./m² 20 DAT) | | | (300) | (310) | (380) | | 61 |

A review of the above test results shows that all treatments applied at 5 DAT produced complete weed control. The yields from the lower rates of Herbicide A were outstanding with the 5 DAT treatments. The The field plots were overseeded with barnyardgrass (E. crusgalli) at 2 kgs/ha. Treatments were replicated four times. Data shown in Table 4 are from observations 36 DAT.

Table 4

| Treatment Herbicide | DAT | Rate kg/ha | Observations-36 DAT % Weed Control Grass Ec and Ecol | Sedges Cd,Ci,Fl | Broadleaf Mv,Sz | Crop Injury (%) | Yield (% of H.W. Check) |
|---|---|---|---|---|---|---|---|
| A | 5 | .25 | 100 | 100 | 100 | 0 | 129 |
| " | " | .5 | 100 | 100 | 100 | 0 | 136 |
| " | " | 1.0 | 100 | 100 | 100 | 0 | 123 |
| " | " | 2.0 | 100 | 100 | 100 | 60 | 101 |
| " | 14 | .25 | 60 | 60 | 50 | 0 | 90 |
| " | " | .5 | 80 | 50 | 50 | 0 | 97 |
| " | " | 1.0 | 80 | 60 | 60 | 0 | 100 |
| " | " | 2.0 | 80 | 60 | 60 | 30 | 97 |
| B | 5 | 1.0 | 100 | 100 | 100 | 0 | 115 |
| " | " | 1.5 | 100 | 100 | 100 | 0 | 110 |
| " | " | 3.0 | 100 | 100 | 100 | 0 | 100 |
| " | 14 | 1.0 | 0 | 0 | 0 | 0 | 82 |
| " | " | 1.5 | 0 | 0 | 0 | 0 | 86 |
| " | " | 3.0 | 50 | 50 | 50 | 0 | 94 |
| H.W. Check (2×) | | | 0 | 100 | 80 | 0 | 100 (3163 kg/ha) |
| Weedy Check (No./m² 20 DAT) | | | (240) | (370) | (500) | 0 | 51 |

For both Herbicides A and B complete control of all weeds resulted at rate of application of herbicide applied 5 DAT. Weed control for 14 DAT application dropped off for Herbicide A in this test, but for Herbicide B the control was nil at the 1.0 and 1.5 kgs/ha rates and only 50% at the 3.0 kgs/ha rate. These results illustrate more weed control with Herbicide A when applied at 14 DAT than with Herbicide B. Moreover, for Herbicide B the yield of 82% at 1.0 kg/ha is statistically significantly lower than the hand weeded check.

Even at the 2.0 kgs/ha rate for Herbicide A at 5 DAT, where crop injury was 60%, the rice yield was slightly more than the hand weeded control, and at the same rate 14 DAT, where crop injury was 30%, the yield was only slightly lower than the hand weeded check. The apparent anomaly between high crop injury and lack of yield depression can be explained on the basis of imperfect weed control in the hand weeded check.

EXAMPLE 5

In this example, comparative results are shown for the performance of Herbicides A and B in field tests on both infant and ordinary transplanted rice in clay loam soil having 2.6% organic matter and a waater percolation rate of 1–2 cm/day at the Japanese Association For Advancement of Phyto Regulators Laboratory (JAAPR) in Japan. The rice seedlings were grown to the 1.7 leaf stage for infant seedlings and to the 5.5 leaf stage for ordinary seedlings. Two days after puddling the soil in which the seedlings were to be transplanted, both infant and ordinary seedlings were transplanted into plots 8.5 m².

As indicated in Table 5, Herbicide A was applied to the weeds and rice at the indicated times of 2, 7 and 15 DAT, respectively, and 7 DAT for Herbicide B. At the time of application of the herbicides, the leaf stage of grass weed (lsg) was as follows: 2 DAT (0–1 lsg), 7 DAT (1–1.5 lsg) and 15 DAT (2–2.5 lsg). The weed symbol "Obw" represents "other broadleaf weeds" of unspecified identity. Results presented in Table 5 represent the average of 2 replications.

Table 5

| Treatment Herbicide | Rate Kg/ha | DAT | Ec | Ann. Cyp | % Weed Control Mv | Obw | Ea | Avg. | Injury | Ordinary Seedlings Yield % of H.W.C. | Infant Seedlings Injury | % of H.W.C. |
|---|---|---|---|---|---|---|---|---|---|---|---|---|
| A | .25 | 2 | 100 | 100 | 80 | 100 | 79 | 92 | 0 | 97 | | |
| " | .5 | 7 | 100 | 80 | 62 | 82 | 98 | 84 | 0 | 95 | | |
| " | 1.0 | 15 | 100 | 100 | 62 | 100 | 90 | 90 | 0 | 96 | | |
| " | .25 | 2 | 100 | 100 | 80 | 100 | 87 | 93 | | | 0 | 98 |
| " | .5 | 7 | 100 | 75 | 60 | 83 | 89 | 81 | | | 0 | 99 |
| " | 1.0 | 15 | 100 | 100 | 67 | 96 | 89 | 90 | | | 0 | 102 |
| B | 1.5 | 7 | 81 | 99 | 86 | 71 | 93 | 86 | 5 | 92 | | |
| | 1.5 | 7 | 99 | 100 | 66 | 100 | 100 | 93 | | | 10 | 99 |

The data in this field test show that Herbiicide A controlled the weed species Ec in both plots at all rates tested. Ann. Cyp and Obw were also controlled completely at the 0.25 kg/ha rate in both plots and 1.0 kg/ha rate in the ordinary rice seedling plot, and in the infant seedling plots, Ann. Cyp was also controlled at the 1.0 kg/ha rate.

For Herbicide B complete control was reported for Ann. Cyp, Obw and Ea at the higher 1.5 kg/ha rate 7 DAT, with substantially complete control of Ec and Ann. Cyp under the same conditions.

On the basis of the average weed control date for 7 DAT, Herbicide A was at least 3 fold more active than Herbicide B. Moreover, Herbicide A, at 0.25 kg/ha, applied 2 DAT was equal to or superior to Herbicide B at 1.5 kg/ha applied 7 DAT, on Ec, Ann. Cyp, Obw and in average weed control for both ordinary and infant seedlings and the yields were essentially the same.

Injury to neither ordinary nor infant seedlings occurred in the above field tests with Herbicide A. All treatments in this test produced rice yields comparable to a handweeded control.

EXAMPLE 6

In this example, the efficacy of Herbicide A is presented for a variety of weeds in the presence of ordinary and infant transplant rice. In this example, tests were conducted at the said JAAPR Lab at different times of the year. "Early season" transplants were made in April and "Normal season" transplants were made in July. The size of the transplants at the respective seasons were:

| Season | Seedling Type | Plant Height (cm) | Leaf Stage |
|---|---|---|---|
| Early | Ordinary | 16.5 | 4.5 |
| Early | Infant | 9.1 | 2.4 |
| Normal | Ordinary | 41.7 | 5.3 |
| Normal | Infant | 14.7 | 1.9 |

The soil used in these tests was a clay loam with 2.3% organic matter and had a percolation rate of 3 cm/day. Duplicate treatments were used. At the time of application of the herbicide, the status of the grass (EC) was as follows:

| DAT | Leaf Stage | |
|---|---|---|
| | Early Season | Normal Season |
| −2* | Preemergence | Preemergence |
| 3 | 0–1 | 0–1 |
| 7 | | 1.2–1.8 |
| 12 | 1–1.5 | |

Results of these tests are shown in Table 6

*"−2" means 2 days before transplanting rice. The primary purpose of the experimental work in this example is to compare relative herbicidal activity of Herbicides A and B against the weeds shown in Table 7; most of these weeds were not available for tests with transplanted rice. Although the relative selectivity of these herbicides in upland rice is also evident, that aspect of the tests is more or less incidental to the purpose of this example.

In this example, rice seeds and seeds of the weeds shown in Table 7 were sown in Ray silt loam soil at a depth of 0.5 inch (1.27 cm) in containers for the soil in a greenhouse. Herbicides A and B were applied to the surface of the soil at a spray volume equivalent to 20 gals/acre (187.1 liters/hectare), followed by 0.5 in (1.27 cm) of overhead irrigation. Temperature and relative humidity in the greenhouse were on the order of 85°F (29°C) and 75%, respectively. Observations were made at 21–28 days after seeding.

In Table 7 are shown the average rates of herbicide required to cause a growth reduction of 85% of the weeds ("$GR_{85}$"), and the average rate of herbicide required to cause a growth reduction of 15% ("$GR_{15}$") of the rice plants (Oryza sativa, "Os", variety Bluebelle).

The date in Table 7 show that both herbicides are selective for most of the weeds tested in upland direct-seeded rice. Although Herbicide B is slightly more Table 6

| Herbi-cide | Growing Season | Treatment Rate kg/ha | DAT | % Weed Control | | | | | | | | | | Rice Seedling Injury (%) | |
|---|---|---|---|---|---|---|---|---|---|---|---|---|---|---|---|
| | | | | Ec | Cd | Mv | Ri | Et | Lp | Obw | Ea | Sp | Cs | Sh | Ordinary | Infant |
| A | Early | .5 | −2 | 100 | 100 | 95 | 100 | 95 | 100 | 100 | 100 | | | | 10 | |
| " | " | 1.0 | " | 100 | 100 | 100 | 100 | 95 | 100 | 100 | 100 | | | | 10 | |
| " | " | .5 | 3 | 100 | 100 | 95 | 100 | 70 | 100 | 100 | 100 | | | | 0 | |
| " | " | 1.0 | " | 100 | 100 | 100 | 100 | 95 | 100 | 100 | 100 | | | | 5 | |
| " | " | .5 | 12 | 100 | 100 | 95 | 100 | <40 | 85 | 100 | 100 | | | | 0 | |
| " | " | 1.0 | " | 100 | 100 | 95 | 100 | 70 | 95 | 50 | 100 | | | | 0 | |
| " | Normal | .5 | −2 | 100 | 100 | 100 | 100 | 100 | 100 | 100 | 100 | <40 | 100 | 100 | 25 | |
| " | " | 1.0 | " | 100 | 100 | 100 | 100 | 100 | 100 | 100 | 100 | <40 | 100 | 100 | 30 | |
| " | " | .5 | 3 | 100 | 100 | 100 | 100 | 100 | 100 | 100 | 100 | <40 | 100 | 100 | 15 | |
| " | " | 1.0 | " | 100 | 100 | 100 | 100 | 100 | 100 | 100 | 100 | <40 | 100 | 100 | 15 | |
| " | " | .5 | 7 | 95 | 100 | 95 | 100 | 100 | 100 | 100 | 100 | <40 | 100 | 100 | 5 | |
| " | " | 1.0 | " | 100 | 100 | 100 | 100 | 100 | 100 | 100 | 100 | <40 | 100 | 100 | 10 | |
| " | " | .5 | −2 | 100 | 100 | 100 | 100 | 100 | 100 | | 100 | <40 | 100 | 100 | | 20 |
| " | " | 1.0 | " | 100 | 100 | 100 | 100 | 100 | 100 | | 100 | <40 | 100 | 100 | | 40 |
| " | " | .5 | 3 | 100 | 100 | 100 | 100 | 100 | 100 | | 100 | <40 | 100 | 100 | | 15 |
| " | " | 1.0 | " | 100 | 100 | 100 | 100 | 100 | 100 | | 100 | <40 | 100 | 100 | | 20 |
| " | " | .5 | 7 | 100 | 100 | 70 | 100 | 100 | 100 | | 100 | <40 | 100 | 100 | | 10 |
| " | " | 1.0 | " | 100 | 100 | 85 | 100 | 100 | 100 | | 100 | <40 | 100 | 100 | | 10 |

The data presented in Table 6 show that Herbicide A was very effective on all weeds in the test except Sagittaria (Sp). It appears that this herbicide was slightly more toxic to both weeds and rice when applied in the normal season than when applied in the early season. No difference was noted between infant and ordinary seedlings with regard to rice toxicity, but it appears that the preemergence treatments were somewhat more toxic to rice than later treatments.

The data in Table 6 illustrate an important feature and benefit of Herbicide A, viz., that it may efficaciously be applied over a wide application period, i.e., from 2 days before transplanting to 12 DAT.

EXAMPLE 7

In a further comparative study of the preemergence activity of Herbicides A and B, a variety of weeds and upland direct-seeded rice were tested under greenhouse conditions. The present invention is not concerned with the use of Herbicide A in direct-seeded selective than Herbicide A for the particular spectrum of weeds used in this type of rice culture. This example further illustrates the differences between Herbicides A and B when used in different rice cultures. Experience with these two herbicides has shown Herbicide A to be more selective than Herbicide B in transplant rice cultures.

Even in direct-seeded rice cultures, Herbicide A has been found to be significantly more active than Herbicide B. In this Example, it is noted that the weeds Cc and Ce appear to be resistant to Herbicide A, whereas the Ce weed also resists Herbicide B.

Table 7

| Plant Species | Avg. Rate for $GR_{85}$ | | | | No. of Tests |
|---|---|---|---|---|---|
| | Herbicide A | | Herbicide B | | |
| | Lbs/Ac | Kgs/Ha | Lbs/Ac | Kgs/Ha | |
| Ec | .078 | .087 | .188 | .211 | 8 |
| Ds | .078 | .087 | ≥ 625 | ≥ .701 | 8 |
| Bp | .094 | .105 | .375 | .420 | 8 |

Table 7-continued

| Plant Species | Avg. Rate for GR₈₅ | | | | |
| --- | --- | --- | --- | --- | --- |
| | Herbicide A | | Herbicide B | | No. of |
| | Lbs/Ac | Kgs/Ha | Lbs/Ac | Kgs/Ha | Tests |
| Ei | .016 | .018 | .031 | .035 | 1 |
| Cc | .50 | .560 | .875 | .981 | 4 |
| Ci | .031 | .035 | .031 | .035 | 3 |
| Ce | ≥.50 | .560 | >2.0 | >2.242 | 2 |
| Ar | .375 | .420 | .375 | .420 | 4 |
| Po | .375 | .420 | .875 | .981 | 3 |
| Jd | .063 | .071 | .125 | .140 | 1 |
| | | Avg. Rate for GR₁₅ | | | |
| Os | .375 | .420 | ≥1.0 | ≥1.121 | 8 |

EXAMPLE 8

As will be appreciated by those skilled in the art, residual weed control of greater than 30 days from date of transplanting is highly desirable for a rice herbicide; otherwide, additional herbicide applications, or else hand weeding, may be required to obtain maximum rice yields.

This example describes the results of tests conducted at the JAAPR Laboratory in Japan to determine the comparative residual effect of Herbicide A vis-a-vis that of commercial rice herbicides in Japan. Results of these tests are shown in Table 8.

In the tests according to this example, the test weed species *Echinochloa crusgalli* (Ec) and *Rotala indica* (Ri), were grown in clay loam soil having 2.3% organic matter and a percolation rate of 3 cm/day for 2 days. Herbicide A was applied to the weeds at an expected use rate of about 0.67–1.34 lbs/ac (0.75–1.5 kgs/ha) and the commercial rice herbicides, whose active ingredients are identified below, were applied at their indicated expected use rates:

| Herbicide | | Rate | |
| --- | --- | --- | --- |
| | | Lbs/Ac | Kgs/Ha |
| C | 2,4,6-trichlorophenyl-4'-nitrophenyl ether | 2.4–4.82 | 2.7–5.4 |
| D | 2,4-dichlorophenyl-4' nitrophenyl ether | 1.88–3.75 | 2.1–4.2 |
| E | Pentachlorophenol | 6.70–13.39 | 7.5–15.0 |
| F | 2,4-dichlorophenyl-3'-methoxy-4'-nitrophenyl ether | 1.88–3.75 | 2.1–4.2 |
| G | p-chlorobenzyl-N,N-diethylthiolcarbamate and 2,4-bis-(ethylamino)-6-(methylthio)-s-triazine | 1.88+0.40–3.75+0.80 | 2.1+0.45–4.2+0.9 |

Table 8

| Plant Species | Length of Residual Activity | | |
| --- | --- | --- | --- |
| | Fair (11–20 days) | Long (21–30 days) | Very Long (over 30 days) |
| Ec | C, D, E | F | A, G |
| Ri | C, D, E | F | A, G |

Reference to the data in Table 8 shows that of the rice herbicides tested only A and G had residual activities lasting over 30 days. In this connection, it will be noted that the combined amount of active ingredients in Herbicide G was considerably greater than the amount of active ingredient in Herbicide A. Moreover, the triazine component in Herbicide G undoubtedly contributes to the long residual activity thereof. However, the usefulness of Herbicide G is limited by the fact that it cannot safely be applied prior to 10–20 DAT. In contrast, it has been shown hereinabove that Herbicide Aa can safely be applied preemergence, e.g., 2 days before transplant, (Table 6) or postemergence, e.g., 14 DAT (Table 4), or any time in between.

EXAMPLE 9

In this example, additional tests were run to compare the relative soil life of Herbicides A and B under greenhouse conditions.

In the soil life tests, a standardized procedure involving a series of bioassay periods, or cycles, was used. In the procedure, an arbitrary, selected mixture of four grasses, four broadleaf weeds and a sedge were seeded into Ray silt loam soil previously prepared and treated with the herbicide under test and periodically watered by sub-irrigation. After a six-week bioassay period, (i.e., the first cycle), the plants were evaluated visually for herbicidal activity. That soil in which at least 75% of three or more grass and/or broadleaf species or of the sedge alone were controlled at the end of the cycle, was advanced to a second cycle, or six-week bioassay period. The second cycle involved the same procedure as the first cycle, except that additionally, the equivalent of 50 lbs/ac (56.05 Kgs/ha) of nitrogen was mixed into the cover layer of the soil which was reseeded with the mixture of plants mentioned earlier. The plants were evaluated for herbicidal activity at the end of this six-week period and, again, the soil in which at least 75% of the grasses or broadleaf species or of the sedge alone were controlled was advanced to a third cycle. The foregoing procedure was repeated until herbicidal activity fell below that required for initiation of a new cycle.

For purposes of the soil life tests, the following spectrum of plants were used as indicators: pigweed, annual morning glory, smartweed, cocklebur, Italian ryegrass, crop rye, sorghum, quack grass and nutsedge.

Table 9

| Treatment | | |
| --- | --- | --- |
| Herbicide | Application Rate | Soil Longevity (Weeks) |
| A | 5 lbs/Ac (5.605 kg/ha) | 29 |
| B | " | 20 |

The soil longevity data in Table 9 indicates that Herbicide A would have residual preemergence activity for a period of time about 50% longer than that for Herbicide B when used at equal rates.

EXAMPLE 10

In view of the importance of fish toxicological considerations, tests were conducted, using carp according to the Japanese protocol, to compare toxicity data for Herbicides A and B; results of those tests are shown in Table 10.

Table 10

| Herbicide | Time in Hours | Medium Lethal Concentration (PPM) |
| --- | --- | --- |
| A | 48 | 1.8 |
| | 96 | 1.4 |
| B | 48 | 1.0 |

Table 10-continued

| Herbicide | Time in Hours | Medium Lethal Concentration (PPM) |
|---|---|---|
| | 96 | 0.76 |

The above data indicate that Herbicide A is only about one-half as toxic as Herbicide B with respect to carp. Since the expected use rate of Herbicide A is about one-third that of Herbicide B, and the above fish toxicology data shows Herbicide A to be about one-half as toxic to carp as Herbicide B, then Herbicide A should be only about one-sixth as toxic as Herbicide B in the field.

The general importance and special significance of the foregoing data showing Herbicide A to be more versatile and generally superior to Herbicide B with respect to herbicidal efficacy in transplant rice and fish toxicology will be more appreciated when it is recognized that Herbicide B has been cleared for use in rice in major rice-growing countries of the world, including, e.g., Taiwan, Japan, Korea, Philippines, Ceylon and other countries. In fact, Herbicide B has been officially established as the single chemical preemergence rice herbicide standard in Taiwan.

The herbicidal compositions of this invention comprise the active ingredient and one or more herbicidal adjuvants, which can be solid or liquid extenders, carriers, diluents, conditioning agents and the like. Preferred herbicidal compositions containing the active ingredient of this invention have been developed so that the active ingredients can be used to the greatest advantage to selectively inhibit the growth of undesirable plants, both monocotyledons and dicotyledons, such as sedges, broadleaf weeds and grasses, including barnyardgrass in the presence of transplanted rice. The preferred compositions comprise certain wettable powders, aqueous suspensions, dust formulations, granules, emulsifiable oils and solutions in solvents. In general, these preferred compositions can all contain one or more surface-active agents.

Surface-active agents which can be used in the herbicidal compositions of this invention are set out, for example, in Searle U.S. Pat. No. 2,426,417; Todd U.S. Pat. No. 2,655,447; Jones U.S. Pat. No. 2,412,510; and Lenher U.S. Pat. No. 2,139,276. A detailed list of such agents is also set forth by J. W. McCutcheon in "Chemical Industries", November 1947, page 811 et seq., entitled "Synthetic Detergents" and "Detergents and Emulsifiers — Up to Date" (1962), by J. W. McCutcheon, Inc. In general, less than 15 parts by weight of the surface-active agent is present per 100 parts by weight of the herbicidal composition.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and silicate. Examples of such extenders include kaolinites, attapulgite clay and synthetic magnesium silicate.

Preferred wetting agents are alkyl benezene and alkyl naphthalene sulfonates, fulfated fatty alcohols, amines or acid amides; long chain acid esters of sodium isothionate, esters of sodium sulfosuccinate, sulfated or sulfonated fatty acid esters, petroleum sulfonates, sulfonated vegetable oils and detertiary acetylinic glycols. Preferred dispersants are methyl cellulose, polyvinyl alcohols, sodium lignin sulfonates, polymeric alkyl naphthalene sulfonates, sodium naphthalene sulfonate, polymethylene bisnaphthalenesulfonate and sodium N-methyl-N-(long chain acid) taurates.

The wettable powders compositions of this invention usually contain from about 5 to about 95 parts of active ingredient, from about 0.25 to about 3.0 parts of wetting agent, from about 0.25 to about 7 parts of dispersant and from about 4.5 to about 94.5 parts of inert solid extender, all parts being by weight of the total composition. Where required from about 0.1 to 2.0 parts by weight of the solid inert extender can be replaced by a corrosion inhibitor or anti-foaming agent or both.

Aqueous suspensions are usually prepared by mixing together an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed coverage is very uniform.

Dusts are dense finely-divided particulate compositions which are intended for application to the soil in dry form. Dusts are characterized by their free-flowing and rapid settling properties so that they are not readily wind-borne to areas where they are of no value. Dusts contain primarily an active ingredient and a dense, free-flowing, finely-divided particulate extender. However, their performance is sometimes aided by the inclusion of a wetting agent such as those listed hereinbefore under wettable powder compositions; convenience in manufacture frequently demands the inclusion of an inert, absorptive grinding aid. Suitable class of grinding aids are natural clays, diatomaceous earth and synthetic minerals derived from silica or silicate. Preferred grinding aids include attapulgite clay, diatomaceous silica, synthetic fine silica and synthetic calcium and magnesium silicates.

The inert finely-divided solid extender for the dusts can be of vegetable or mineral origin. The solid extenders are characterized by possessing relatively low surface areas and are poor in liquid absorption. Suitable inert solid extenders for herbicidal dusts include micaceous talcs, pyrophyllite, dense kaolin clays, ground calcium phosphate rock and tobacco dust. The dusts usually contain from about 0.5 to 99 parts active ingredient, 0 to 50 parts grinding aid, 0 to 3 parts wetting agent and 1 to 99.5 parts dense solid extender, all parts being by weight based on the total weight of the dust.

The wettable powders described above may also be used in the preparation of dusts. While such wettable powders could be used directly in dust form, it is more advantageous to dilute them by blending with the dense dust diluent. In this manner, dispersing agents, corrosion inhibitors, and anti-foam agents may also be found as components of a dust.

Emulsifiable oils are usually solutions of active ingredient in water-immiscible solvents together with a surfactant. Suitable solvents for the active ingredient of this invention include hydrocarbons and water-immiscible ethers, esters or ketones. Suitable surfactants are anionic, cationic and nonionic such as alkyl aryl polyethoxy alcohols, alkyl and alkyl aryl polyether alcohols, polyethylene glycol fatty esters, fatty alkyllol amide condensates, amine salts of fatty alcohol sulfates together with long chain alcohols and oil soluble petrolcum sulfonates or mixtures thereof. The emulsifiable oil compositions generally contain from about 5 to 95 parts active ingredient, about 1 to 10 parts surfactant and about 4 to 94 parts solvent, all parts being by weight based on the total weight of emulsifiable oil composition.

Granules are physically stable particulate compositions comprising active ingredient adhering to or distributed through a basic matrix of an inert, finely-divided particulate carrier or extender. In order to aid leaching of the active ingredient from the particulate, the surfactant such as those listed hereinbefore under wettable powders can be present in the composition. The preferred extenders for use herein are dense, aggregates which are adsorptive for the active ingredient; these include limestone, gypsum, expanded shale, sand and extruded granules. These extenders may be used alone or in admixture with other extenders, e.g., powdered clays. Other useful extenders include diatomaceous earth, pearlite, volcanic aggregates, natural clays, pyrophyllites, and vermiculite. Preformed and screened particulate attapulgite or heat-expanded vermiculite and the finely-divided clays such as kaolin clays, hydrated attapulgite or bentonitic clays are useful herein. These extenders are sprayed or blended with the active ingredient to form the herbicidal granules.

The mineral particles which are used in the granular herbicidal compositions of this invention usually have a size range of 10 to 100 mesh, but preferably such that a large majority of the particles have from 14 to 60 mesh with the optimum size being from 16 to 40 mesh. Carriers having substantially all particles between 14 and 80 mesh and at least about 80 percent between 16 and 40 mesh is particularly preferred for use in the present granular compositions. The term "mesh" as used herein means U.S. Sieve Series.

The granular herbicidal compositions of this invention generally contain from about 1 to 30 parts by weight of the active ingredient and about 0 to 5 parts by weight of wetting agent per 100 parts by weight of extender. The preferred herbicidal granular compositions contain from about 2 to 25 parts by weight of active ingredient and about 1 to 3 parts by weight of wetting agent per 100 parts by weight of extender.

The selective herbicidal compositions of this invention can also contain other additaments, for example, fertilizers, other herbicides, pesticides and the like, used as adjuvant or in combination with any of the above-described adjuvants.

Herbicidally-active compounds which may be used in combination with the compound of this invention include but are not limited to: acetanilides such as butachlor, carbamates such as p-chlorobenzyl diethylthiolcarbamate, benzyl N,N-di-sec-butyl thiolcarbamate and S-ethyl hexahydro-1H-azepine-1-carbothiolate; biphenylethers such as 2,4-dichlorophenyl-4'-nitrophenylether and 2,4,6-trichlorophenyl-4'-nitrophenylether; benzothiadiazines such as 3-isopropyl-1H-2,1,3-benzothiadiazin-(4)-3H-one 2,2-dioxide; anilides such as 3',4'-dichloropropionanilide, oxadiazolines such as 2-t-butyl-4-(2,4-dichloro-5-isopropyloxyphenyl)-5-oxo-1,3,4-oxadiazoline; triazines such as 2,4-bis (ethylamino)-6-(methylthio)-s-triazine, 2,4-bis (isopropylamino)-6-(methylthio)-s-triazine, 2-(ethylamino)-4-(N-ethyl-N-isobutenylamino)-6-(methylthio)-s-triazine and 2-(1,2-dimethylpropylamino)-4-ethylamino-6-methylthio-1,3,5-triazine; phenols such as pentachlorophenol; sulfanilamides such as 3,5-dinitro-$N^4$, $N^4$-dipropylsulfanilamide and phenoxies such as 2,4-dichlorophenoxy acetic acid, 2-methyl-4-chlorophenoxy acetic acid, 2,4,5-trichlorophenoxyacetic acid and their salt and ester derivatives.

The herbicide of this invention is suitably applied either preemergently or postemergently to the growth medium or to the plant, e.g., to the soil or the flooded area after the transplant has been fixed. The active ingredient is suitably applied at a rate of about 0.05 to about 4 or more lbs. per acre (i.e., from about 0.06 to about 4.48 or more kgs/hectare). In more general applications, a preferred application range is from about 0.25 lb/acre to about 1.5 lb/acre (i.e., from about 0.28 kg/hectare to about 1.68 kgs/hectare), and the most preferred and usually recommended use rate is about 0.5 lb/acre (about 0.56 kg/hectare). The amount of herbicide used is dependent upon the organic content of the soil. This is within the knowledge of those skilled in the art.

In further particular, when operating in accordance with the present invention, herbicidally effective amounts of the active ingredient, N-(butoxymethyl)-6'-tert-butyl-2-chloro-o-acetotoluidide, or its admixture with other herbicidally-active compounds, are dispersed in or on soil and/or applied to aboveground or flood-water portions of plants in any convenient fashion. Application to the soil or growth media can be carried out simply by admixing with the soil, by applying to the surface of the soil and thereafter dragging or discing into the soil to the desired depth, or by employing a liquid carrier to accomplish penetration and impregnation. The application of liquid and particulate solid herbicidal formulations to the surface of soil or above-ground or flood-water portions of plants can be carried out by conventional methods, e.g., power dusters, boom and hand sprayers and spray dusters. The formulations can also be applied from airplanes as a dust, a spray or granules because of their effectiveness at low dosages. In a further method, the distribution of the active ingredient(s) in soil can be carried out by admixture with the water employed to irrigate or flood the soil. In such procedures the amount of water can be varied according to the porosity and water-holding capacity of the soil to obtain the desired depth of distribution of the herbicide.

The term "soil" as employed herein is intended in its broadest sense to include all conventional "soils" as defined in Webster's New International Dictionary, Second Edition, Unabridged (1961). Thus, the term "soil" refers to any substance or media in which vegetation may take root and grow, and is intended to include not only earth, but also compost, manure, muck, humus, sand and the like adapted to support plant growth.

The terms "plant", "weeds" or "undesirable vegetation" as used herein and in the appended claims means dormant seeds, germinant seeds, germinative seeds, emerging seedlings and established vegetation including the roots and above-ground portions.

While the illustrative embodiments of the invention have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein, but, rather, the claims be construed as encompassing all the features of patentable novelty which reside in the present invention including all features which would be treated as equivalents thereof by those skilled in the art to which the invention pertains.

I claim:

1. Method for selectively inhibiting the growth of undesirable vegetation in the presence of transplanted rice which comprises applying to the locus thereof a herbicidally effective amount of the compound N-(butoxymethyl)-6'-tert-butyl-2-chloro-o-acetotoluidide.

2. Method according to claim 1 wherein said compound is applied in an amount corresponding to from about 0.25 lb/acre to about 3.0 lb/acre.

3. Method according to claim 1 wherein said compound is applied in an amount corresponding to from about 0.25 lb/acre to about 1.5 lbs/acre.

4. Method according to claim 1 wherein said undesirable vegetation comprises monocotyledons and dicotyledons.

5. Method according to claim 1 wherein said compound is incorporated into said growth medium prior to emergence of said undesired vegetation.

6. Method according to claim 1 wherein said compound is applied to the surface of said growth medium prior to emergence of said undesired vegetation.

7. Method according to claim 1 wherein said compound is postemergently applied to said vegetation.

8. Method according to claim 4 wherein said monocotyledons are grasses including: *Brachiaria platyphylla*, *Digitaria sanguinalis*, *Echinochloa* spp, *Eleusine indica* and *Leptochloa* spp and *Setaria* spp.

9. Method according to claim 4 wherein said monocotyledons are sedges including: *Cyperus difformis*, *Cyperus iria*, *Cyperus serotinus*, *Eleocharis acicularis*, *Eleocharis kuroguwai*, *Fimbristylis* spp, *Scirpus hotarui* and *Scirpus* spp.

10. Method according to claim 4 wherein said monocotyledons are broadleaf weeds including *Commelina communis*, *Alisma canaliculatum*, *Aneilema japonica* and *Monochoria vaginalis*.

11. Method according to claim 4 wherein said dicotyledons are broadleaf weeds including: *Ammannia* spp, *Amaranthus retroflexus*, *Elatine triandra*, *Jussiaea decurrens*, *Lindernia pyxidaria*, *Rotala indica*, *Sphenoclea zeylanica* and *Portulaca oleracea*.

12. Method according to claim 8 wherein said grass is selected from the group consisting of *Echinochloa crusgalli* and *Echinochloa colonum*.

13. Method according to claim 9 wherein said sedge is selected from the group consisting of *Cyperus difformis* and *Cyperus iria*.

14. Method according to claim 10 wherein said monocotyledonous broadleaf weed is *Monochoria vaginalis*.

15. Method according to claim 11 wherein said dicotyledonous broadleaf weed is *Rotala indica*.

* * * * *